(12) United States Patent
Abrams et al.

(10) Patent No.: US 8,572,507 B2
(45) Date of Patent: Oct. 29, 2013

(54) SYSTEMS AND METHODS FOR INTERACTING WITH DYNAMIC PROTOCOLS

(75) Inventors: Kevin Abrams, Loves Park, IL (US); Douglas Hayworth, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 209 days.

(21) Appl. No.: 13/049,969

(22) Filed: Mar. 17, 2011

(65) Prior Publication Data
US 2011/0289442 A1    Nov. 24, 2011

Related U.S. Application Data

(60) Provisional application No. 61/346,119, filed on May 19, 2010.

(51) Int. Cl.
G06F 3/048    (2013.01)
G06F 3/00     (2006.01)

(52) U.S. Cl.
USPC .......... 715/772; 715/764; 715/771; 715/810; 715/817; 715/818

(58) Field of Classification Search
USPC ............... 715/764, 771, 772, 810, 817, 818
See application file for complete search history.

(56) References Cited

U.S. PATENT DOCUMENTS

| | | | |
|---|---|---|---|
| 7,941,565 B2 * | 5/2011 | Vail | 709/250 |
| 2007/0124278 A1 * | 5/2007 | Lewis et al. | 707/2 |
| 2008/0300993 A1 | 12/2008 | Rozenblatt | |
| 2009/0138415 A1 * | 5/2009 | Lancaster | 706/11 |
| 2009/0259689 A1 | 10/2009 | Do et al. | |
| 2009/0313570 A1 * | 12/2009 | Po | 715/772 |
| 2009/0316977 A1 * | 12/2009 | Juncker et al. | 382/133 |

* cited by examiner

*Primary Examiner* — Nicholas Augustine
(74) *Attorney, Agent, or Firm* — Thompson Hine LLP

(57) ABSTRACT

Systems and methods to provide users with a user interface at the point of use that provides customizable, interactive protocols, where a protocol is typically an instruction set, procedure, or methodology.

13 Claims, 13 Drawing Sheets

SYSTEMS AND METHODS FOR INTERACTING WITH DYNAMIC PROTOCOLS

This application claims priority to U.S. Application Ser. No. 61/346,119 filed May 19, 2010.

The systems and methods provide users customizable, interactive protocols, where a protocol is typically an instruction set, defined procedure, or methodology, often used in a laboratory setting. A user interface provides protocol users with increased functionality and flexibility, beyond that of simple instruction or procedure manuals. In embodiments, users interact with the presented protocols, using the provided interface to step through each stage of a selected protocol. In embodiments, users are able to select topics for additional information. For example, the user interface incorporates hypertext links within stages of protocols, such that users can select a link to retrieve additional information related to the protocol (e.g., detailed more descriptions individual steps of the protocol or equipment used in the protocol) as desired. In other embodiments, the user interface supports tools (e.g., timers, notepads) associated with various steps to optimize protocol processing and reduce errors.

Generally, laboratory environments require complex research protocols, chemical procedures, and complicated equipment instructions. Many of the standard protocols can be modified for the individual needs of the various users. For example, protocols are customized based upon availability of alternative equipment, material costs, technician training, time constraints or simply individual user preferences. The methods are capable of allowing a user to individualize protocols based upon user preferences, including user environment, user limitations, cost or time constraints, and any other reasons for varying protocols. In embodiments, users are able to create, modify, store, and share their own protocols. In embodiments, users are able to select desired protocols from a set or library of defined protocols.

The disclosed systems and methods are described with respect to the research or scientific environment for exemplary purposes only. Implementation of the systems on portable devices facilitates use in a lab environment, allowing users to review protocols proximate to various stations where the protocol is processed. However, the described systems and methods are not limited to the laboratory or other scientific environment, and other uses are possible.

BRIEF DESCRIPTION OF THE DRAWINGS

FIG. 1 depicts an embodiment of a protocol system 100 that provides users with a dynamic interface to one or more protocols. A protocol is an instruction set, such as a procedure or other method. One or more protocols are specified in a data module, also referred to as a module. In an embodiment, a module defines the steps or stages of one or more protocols, and an order or suggested order for the steps. Modules can include text, charts or diagrams, audio, hypertext links or any other data useful for providing a user with protocol-related information, including product and accessory information. In embodiments, modules specify or incorporate interactive functions or features associated with the steps of a protocol or protocols. For example, a step can include related tools, such as timers useful for timed steps, or additional explanation or instructions available upon user selection. The module also specifies an order or a suggested order of steps for a protocol, such that the user is guided through the protocol.

Figure 1:
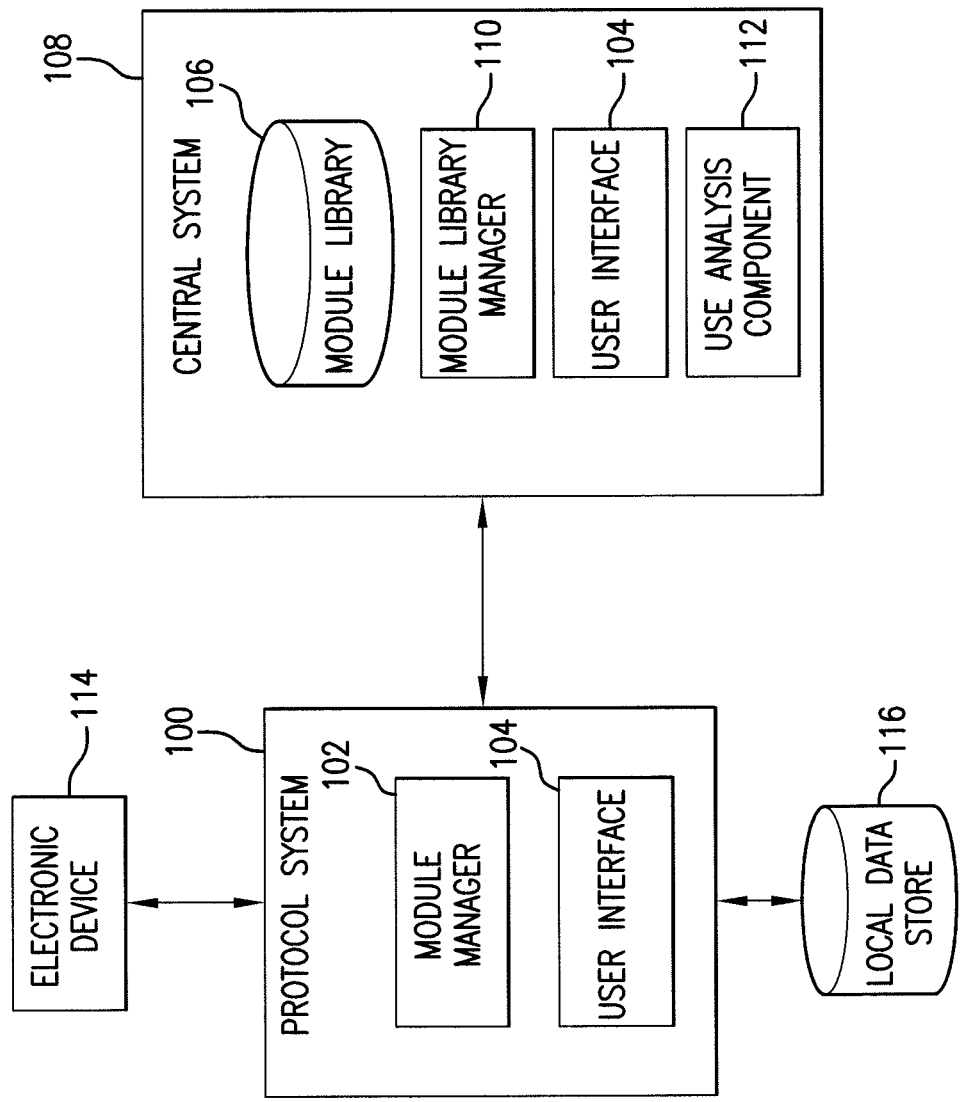
FIG. 1 depicts a block diagram of an embodiment of a protocol interface system.

In embodiments, the protocol system 100 includes a module manager 102 that loads or reads modules to obtain specifications of the protocol or protocols and a user interface 104, such as a graphical user interface (GUI) that enables users to interact with the loaded protocols. The module manager 102 also allows users to delete, update, or copy modules. In embodiments, the module manager 102 identifies the correct module for use, based at least in part by user selections through the user interface 104. The module manager 102 then reads in at least a part of the module. In an embodiment, the module includes directions or information utilized by the user interface 104, such as text to display, audio to present, or additional graphics to demonstrate procedures, etc. The module also includes instructions for user interaction with the module. For example, upon completion of a particular step within the protocol, the module provides information regarding the next step for display by the user interface 104, including the text to be presented, tools to be provided, etc.

The module defines the interactive options associated with the particular protocol, e.g., the text, charts, links or other information associated with one or more steps of a protocol. The module can contain the data values, graphics and other information that will be interpreted by and used by the system and displayed in the user interface 104. Therefore, the system can control any options that may be changed (notes, definitions, adjustment of timers, calculations, ability to skip steps, etc). If saved, the application will write those values to fields within a module, e.g., a database file for later use. The module manager 102 may retrieve or load the entire module at a single time, or may load portions of the module as required or as prompted.

In embodiments, the module manager 102 handles user customization of modules. In certain embodiments, the system allows users to modify or edit modules. For example, a user may enter notes associated with a module or particular steps within a module. These notes can be incorporated into the module, such that the notes are provided to future users of the module. Alternatively, the notes may be associated solely with the individual user that created the notes. For example, a user identifier may be maintained and used to provide personalized information specific to an individual user. In embodiments, users can copy modules and create their own modules. The module manager 102 handles storing of modules. On a mobile device, the module manager 102 can be part of the application. In the online environment, the module manager/creator can be a separate website and interface.

In an embodiment, modules are implemented using a database (e.g., a relational SQL database). For example, each step may be maintained as a data record, including data fields that define text displayed to the user, hypertext links available for the step, available tools or functions (e.g., timers), as well as a link or indicator of the next step and previous step for the protocol. It is apparent that numerous data structures are possible to store the data for individual steps and the relationship among the steps. In embodiments, the database includes records that store user inputs, default timers and any other information associated with the protocol. In such embodiments, the module manager 102 interacts with the database, retrieving the necessary data records and updating data fields as appropriate.

In embodiments, modules are implemented as Extensible Markup Language (XML) data files, including text for display at each step, as well as tagged data specifying hypertext links, available tools, next and previous steps. In these embodiments, the module manager 102 identifies the appropriate XML file for a selected protocol, reads the tagged file and outputs a modified file based upon user input.

The user interface 104 facilitates interaction between the user and the protocol specified by a particular module. The user interface 104 can utilize a display, touch screen, speaker, or any other device useful to communicate protocol information to a user. The user interface 104 obtains user input from a user through any available source or device, e.g., keyboard, touch screen, mouse, microphone, stylus, trackball or any other device for user input. As described, the user interacts with the module in a dynamic manner, facilitating protocol completion, optimization, etc.

In an embodiment, a library or repository of modules is maintained, either locally or accessible via a network. Users can select desired modules from a module library 106. The module manager 102 then loads the selected module for use. The user can create a customized copy of a protocol, modifying existing protocols for the user's individual needs or preferences.

Modules provide significant flexibility in defining protocols. Modules can be used to define protocols for common laboratory preparations, providing step-by-step instructions for creation of e.g., compounds, solutions, reagents, assays, etc. In other embodiments, module protocols describe instructions or procedures for use of scientific products. As one example, a manufacturer provides instructions or best practices for new or common tools, etc. As another example, research protocols or practices are presented to users. In other embodiments, a single module can include multiple protocols.

The protocol system 100 illustrated in FIG. 1 can be implemented using a variety of devices and software components. For example, the protocol system 100 may be implemented as a server application, accessible via a web browser. Alternatively, the protocol system 100 may be accessible through web enabled mobile devices (e.g., the Apple iPhone® or iPad®). In another embodiment, the protocol system 100 is implemented as a software application that may be downloaded to a mobile device, such as smart phones (e.g., iPhone®, BlackBerry®, Droid®), an iPod® touch or a tablet computer (e.g., iPad®). In further embodiments, the system is implemented as a software application that can be installed on desk top or laptop computers. The software application may run in a stand-alone mode, accessing only local memory or local area network (LAN) devices 116. Alternatively, the software application may access a wide area network (WAN), such as the Internet, either for additional modules, updates, or other functionality.

In one embodiment, the system includes or is in communication with a central system 108, accessible via the Internet. In certain embodiments, the central system 108 includes a module library or repository 106, such that individual protocol systems 100 access, download from or upload modules to the library. In one embodiment, the central system 108 includes or utilizes an electronic payment system, where users are charged for download of modules. The central system 108 may also include a module library manager 110 that allows for searches of available modules, storage of new modules, control of module library 106, etc. The module library manager 110 can control module versions and access and edit rights, allowing for updates to modules by users with the requisite authority. For example, authors of modules may define a set or class of individuals with the authority to update modules within the library (e.g. administrators). In one embodiment, the module library manager 110 provides notification to users when modules are modified, allowing users to download the updated modules. In an embodiment, each time a protocol system 100 loads a module, a message is transmitted to the central system 108 to determine if there are updates available. The user may be notified and given the option to download an update, or updates may be retrieved automatically.

In one embodiment, the central system 108 supports a community of users. For example, the central system 108 can include an online forum, where users can exchange information, e.g. regarding particularly useful or recommended modules. Users can provide feedback, suggestions for improvements, complaints, proposed new protocols, as well as any other useful or relevant information. The resulting user generated content provides additional value to users of modules. The forum can be monitored by system developers, and thus provide a method for the user to communicate to interact with others and the system developer. User generated content is amenable to search engines and facilitates trust, acceptance, etc. in potential customers. Users can link to the central system 108 through social networks (e.g., Twitter®, Facebook®, LinkedIn®), receiving updates and notifications of changes to the central system 108 or particular modules. In an embodiment, the central system 108 provides for different levels of users. Users that register with the system, providing information regarding background and protocol use, and offering feedback related to protocols can access additional content and functions. For example, such users may be permitted to store their own customized modules at the central system 108.

The central system 108 can also provide an interface 104 that allows users to define modules. The interface 104 can be provided as a graphical user interface (GUI) through which the user can specify the components of a module to define a particular protocol. The user interface 104 can support text, dynamic interactions, and any other capabilities that would allow users to interact with the user created module. Users can post or upload content to the library of modules. In other embodiments, the module library manager 110 tracks authors of modules, controlling access or updates to such modules based upon authorship and defined access rights. In further embodiments, authors can define access rights, allowing all users to access modules, providing read only rights or edit rights to authored modules.

In a further embodiment, the central system 108 includes a use analysis component 112 that collects usage statistics and information for modules. Data related to usage of particular protocols may be invaluable to manufacturers in marketing of current products, updates or modifications of current products as well as the development of new products. Accordingly, the use analysis component 112 collects data regarding users and the particular modules selected, used, updated, commented upon or with which users otherwise interacted. In one embodiment, the module manager 102 of the protocol system 100 provides data regarding use of modules to the central system 108. In an embodiment, tracking codes, such as a webtrends tracking code, are used to monitor traffic or use of a website, such as the central system web site. A webtrend tracking code is a bit of information added to a web link that allows the source of internet traffic to be determined.

In one embodiment, a manufacturer, retailer, or other vendor utilizes the central system 108 to interact with potential users. The vendor can participate or moderate the user discussions, soliciting feedback, providing support or additional information to users and identifying areas for improvement, including modules, protocols themselves, and vendor products utilized in the protocols (e.g., the forum). In other embodiments, vendors can provide predefined modules incorporating brand or product suggestions. In addition, the modules may include banners, tags or other advertisements for products by the author of the module. A vendor can also embed brand and product information within the modules, incorporating unobtrusive ads and tickers. This may be controlled by the applications, and can be influenced by the module. For example, a certain module for a protein assay may cause the application to display banners or tickers for a new protein assay. A different module may cause the application to display information about a promotion. If the module is modified, the brand and other source indicia can be automatically removed to denote that the module is no longer in the state provided by the module developer.

In one embodiment, the protocol system 100 is capable of communicating, downloading or transmitting data to computers and other electronic devices 114. The protocol system 100 can receive information from devices, such as status of a device (e.g., temperature, in use). The status may be relevant to the protocol and affect the details or order of steps within the protocol. In one embodiment, the protocol system 100 is capable of transmitting data to an electronic device 114, such as transmitting laboratory notes to a central computer network for retention, dissemination, etc. In one embodiment, the protocol system 100 is capable of directing the electronic devices 114, such as setting temperatures, speed or other device features. These communications between the protocol system 100 can be effected by wireless transmissions.

Figure 2:
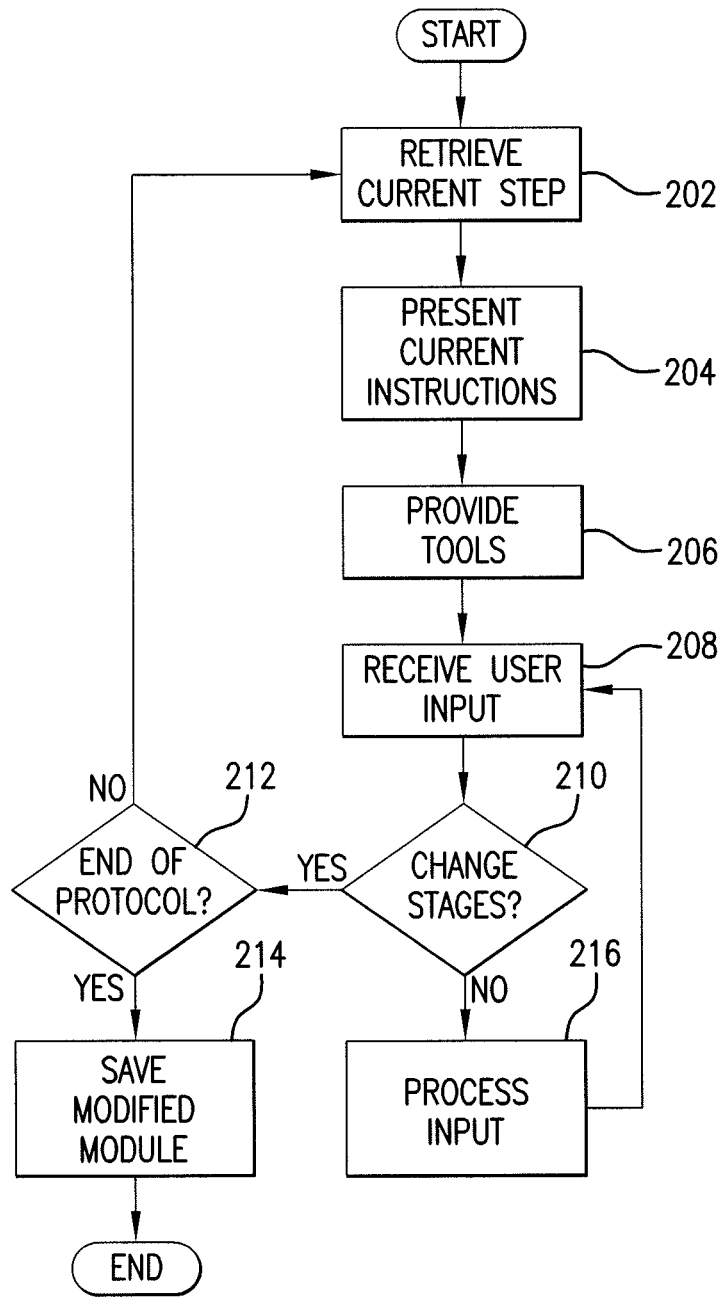
FIG. 2 depicts a flowchart of an exemplary methodology for processing a protocol.

FIG. 2 is a flowchart of an exemplary methodology for processing a protocol with the protocol system 100. At step 202, the first step or stage of the protocol is retrieved from the module. At step 204, the instructions for the current stage are presented to the user, e.g., the text for the step is displayed to the user. For example, a brief description of the stage is displayed on a display screen. In an embodiment, the protocol system 100 includes an audio component, and the user receives audible instructions for the current stage.

At step 206, any associated functions or tools are presented to the user. For example, if the current stage is timed, a timer is presented and may be defaulted to the appropriate length of time for the stage. Users can be provided with a note or text entry tool, such that the user enters notes related to the current stage, or variables that may affect the protocol (e.g., sample volumes, equipment, temperature, humidity, altitude, etc.).

At step 208, user input is received in a myriad of forms. The user may direct the protocol to continue to the next stage, or return to a previous stage. At step 210, a determination is made as to whether the user has selected another stage in the protocol. The user may direct the system to move on to another stage, or alternatively to return to a previous stage within the protocol. In embodiments, the system allows a user to elect the next stage from a selection of available options. Users can be provided with the ability to move through the protocol in the manner in which they choose, to the extent that such freedom does not interfere with the protocol results.

If a change of stage is directed, at step 212, a determination is made as to whether the end of the protocol has been reached. If so, the system can save the module as modified, if necessary at step 214 and the process ends. If the final stage has not been reached, the process returns to step 202, where the current stage is retrieved. If the user does not direct a change of stage at step 210, user input is processed at step 216. Such processing can include setting a timer, input of notes, or other user customization. The process then continues, providing for additional user input and eventual progression to the next stage in the protocol.

Figure 3:
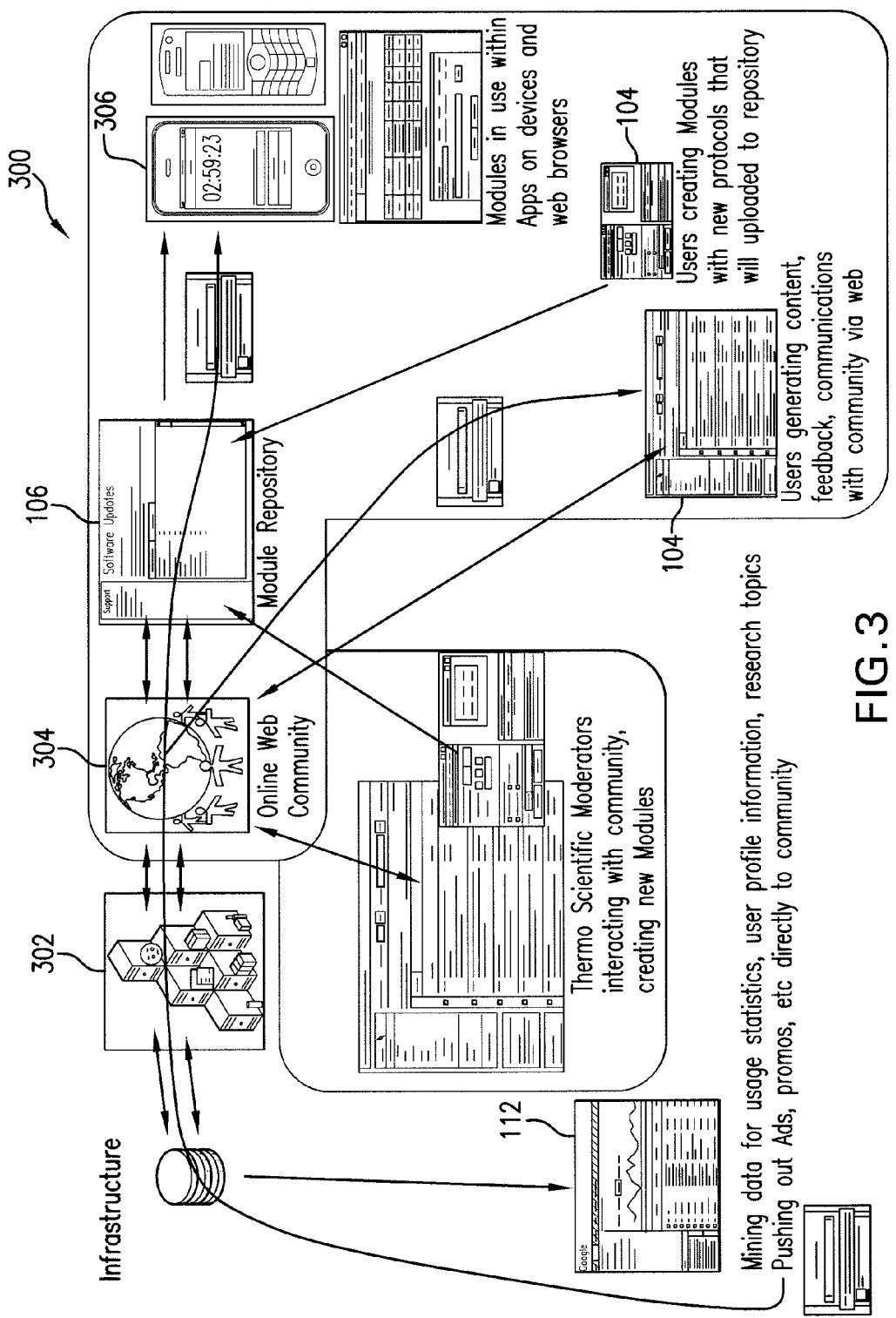
FIG. 3 depicts an infrastructure for an embodiment of the protocol interface system.

FIG. 3 illustrates an exemplary infrastructure 300, where the central system 108 coordinates with one or more protocol systems 100 to provide interactive protocols to users. As shown, a set of servers 302 support an online web community 304 and a module repository or library 106. The online forum 304 can be moderated to provide support and assist in the creation of new modules, enhancing uses for the system. Modules, including both user and administrator created modules, are maintained in a central module repository 106, and may be downloaded to local devices, or alternatively accessed via web browsers (e.g., Microsoft Explorer, Firefox, Apple Safari). As shown, the modules may be downloaded to mobile devices, such as Smart phones, where a protocol system 100 utilizes the modules to provide dynamic protocols to the users. In addition, those users can communicate with the online community 304, as well as creating new modules. The infrastructure allows for data mining, capturing usage statistics, user profiles, research topics, as well as an additional avenue for delivering ads, notices, new releases, promotions, or product news to users.

The user interface 104 of the protocol system 100 can utilize advances in user interface technology to better support customers. For example, increasingly portable devices such as smart phones and tablet computers allow for ease in accessing information regardless of location. The protocol system 100 can be easily transported in the lab environment, providing for access to protocol instructions at each station within the lab.

In an embodiment, user interface 104, whether located at the central system 108, or at the local, protocol system 100, allows users to browse modules based upon module features, including but not limited to, author, subject matter, date of creation, user ratings (e.g., one to five stars), similar modules and the like. The user interface 104 can indicate which modules have already been downloaded by the user, as well as new modules available for download. In other embodiments, the user interface 104 allows the user to search based upon key words or product numbers. The user interface 104 can provide a simple keyboard if the device provides only a touchpad. In an embodiment, the user interface 104 presents modules in a drill down menu, broken into categories and subcategories to allow facilitate finding relevant protocols.

Figure 4:
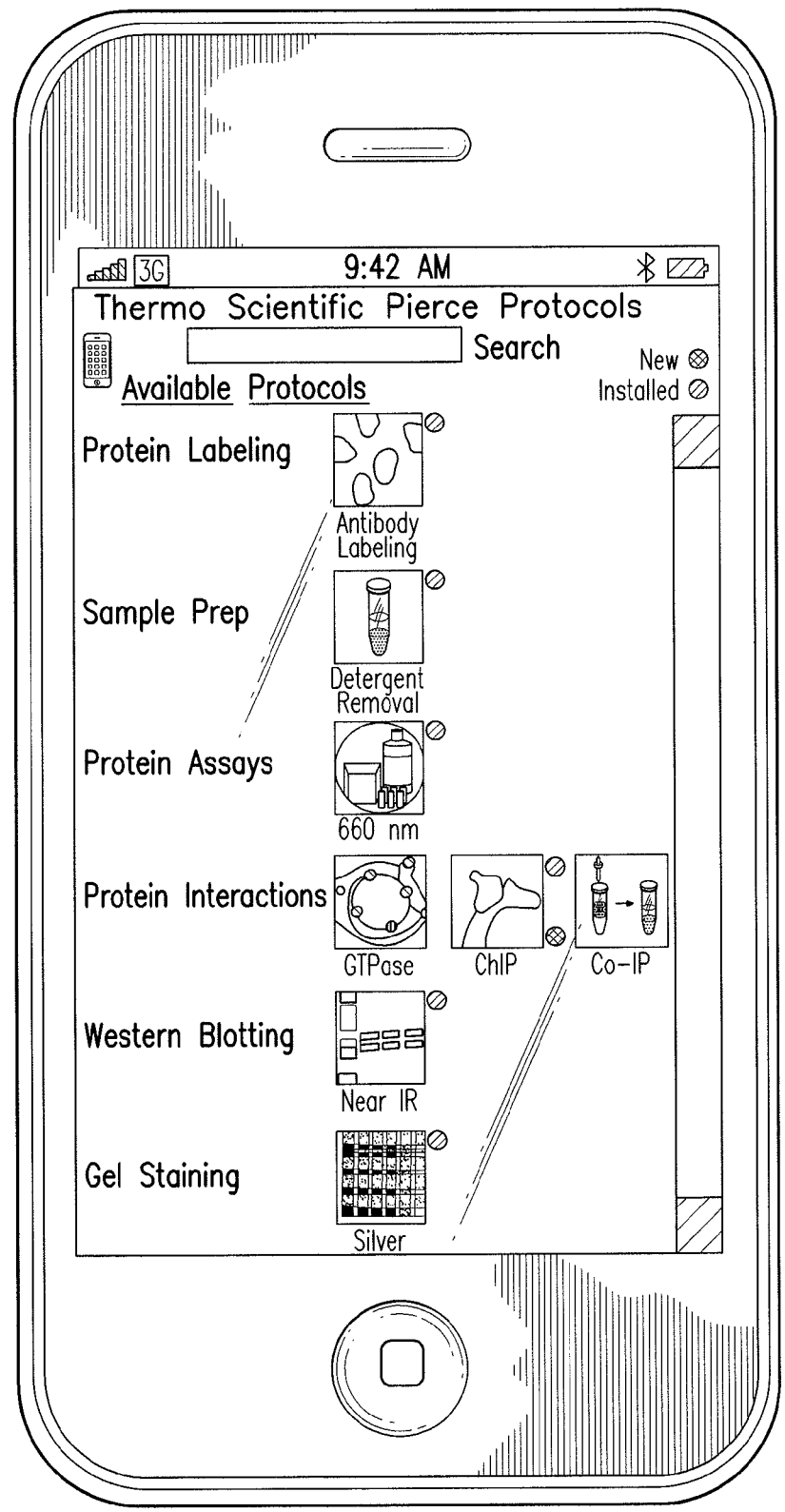
FIG. 4 depicts an exemplary user interface of the protocol interface system.
Figure 5:
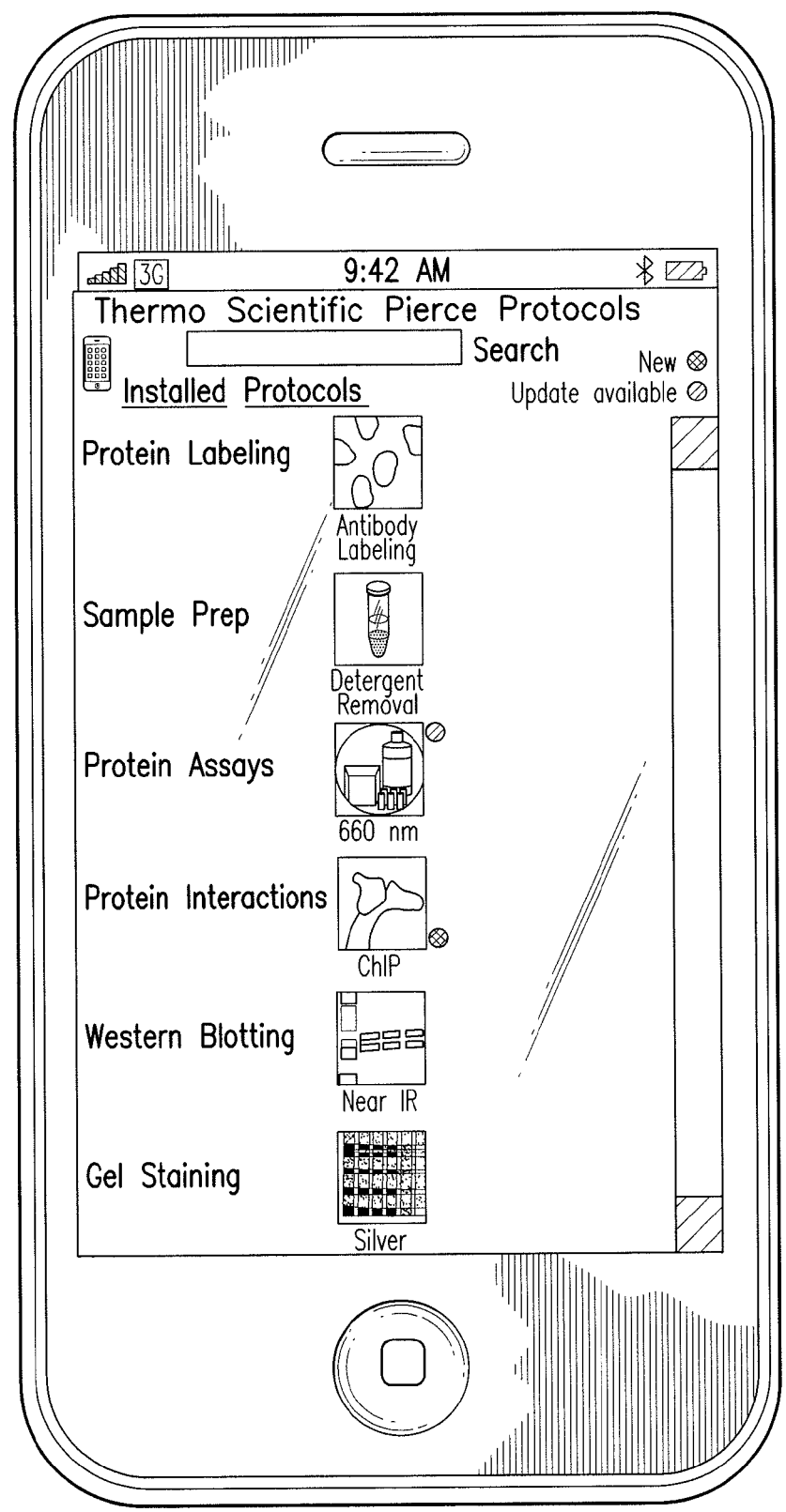
FIG. 5 depicts an exemplary user interface of the protocol interface system.

FIGS. 4-11 depict exemplary screen shots for a user interface 104. As shown in FIGS. 4 and 5, various icons or thumbnails and titles are used to represent individual protocols. In embodiments, the user interface 104 provides users with a mechanism for browsing available protocols, including both those protocols currently downloaded or local to the protocol system 100, as well as those available from a central system 108 or other remote location. As shown in FIG. 4, the user can browse by category, selecting a category to view modules within the category. Icons and names of modules available both locally and at the remote locations with those modules already downloaded are denoted by a flag or other indicator, and a scrollbar available to move through the list. Alternatively, in FIG. 5, the user interface 104 provides only those modules available locally. The user interface 104 can indicate newly available modules, popular modules or highly-rated modules. In further embodiments, users can obtain additional information regarding specific modules (e.g., full title, product numbers, number of steps, author, and necessary equipment) by selecting the particular module, either using a cursor, simply touching the screen, or using any other tool or method for interacting with the system. For example, selecting the search bar brings up a keypad. Users can select individual or sets of modules for download and launch.

Figure 6:
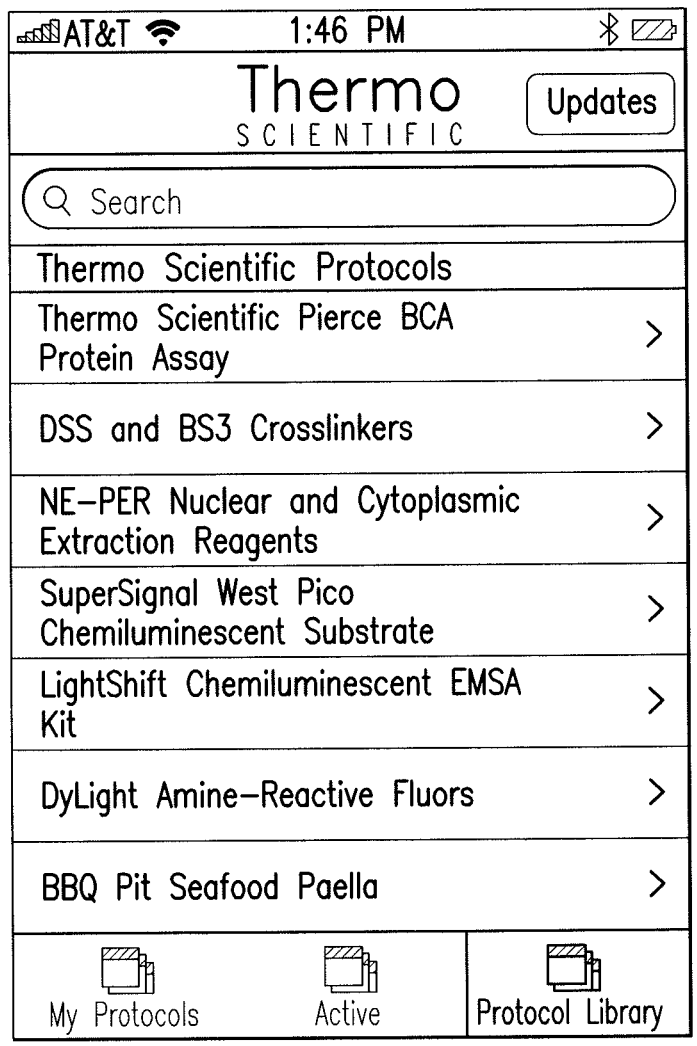
FIG. 6 depicts an exemplary user interface of the protocol interface system.

In another embodiment of the user interface 104 shown in FIG. 6, the user can elect to search different libraries or sets of modules indicated along the bottom of the user interface 104. In the illustrated example, users can elect to view or search "My Protocols" including those protocols resident on the local protocol system 100 or stored at the central system 108, "Active Protocols" that are in progress, and the "Protocol Library" for the library of protocols available from the central system 108.

Figure 7:
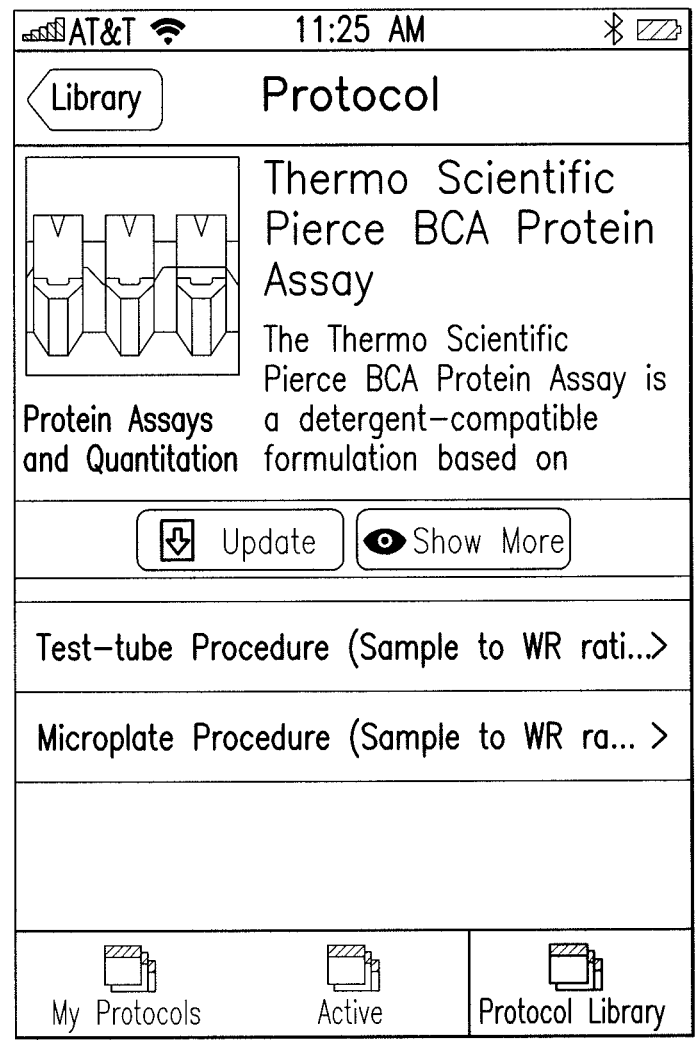
FIG. 7 depicts an exemplary user interface of the protocol interface system.

As illustrated in FIG. 7, upon user selection of a module from the library, the user interface 104 displays a brief description of the particular module along with relevant images. As shown, the user interface 104 can allow users to review additional information, including a more detailed summary, or description of ingredients or equipment required.

Figure 8:
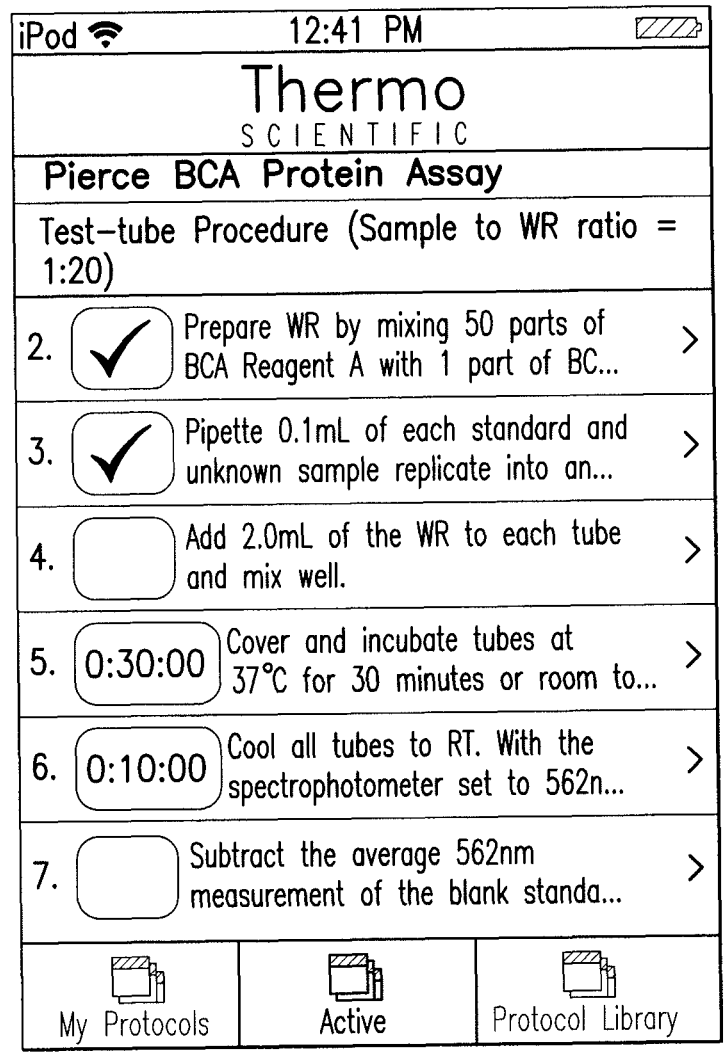
FIG. 8 depicts an exemplary user interface of the protocol interface system.

In an embodiment, upon launching a module, the protocol system 100 provides the user with an interface to the interactive protocol defined by the module. For example, the protocol may provide users with a list or overview of the individual steps make up the protocol, as shown in FIG. 8. Users may interact with the list of steps, selecting specific steps for further information. For example, by tapping or otherwise selecting a step, the user is presented with a detailed description of the step, the necessary equipment, any limitations or other information related to that particular step of the protocol. This additional information may be provided in a simple pop-up window, overlaying a portion of the screen that displays the list of steps, may fill the entire screen, or based upon user selection may fill a portion or whole of the screen. Users also can customize colors. Upon conclusion of a step, the user interface 104 can indicate that the step was completed, as shown in FIG. 8 by a checkmark.

Figure 9:
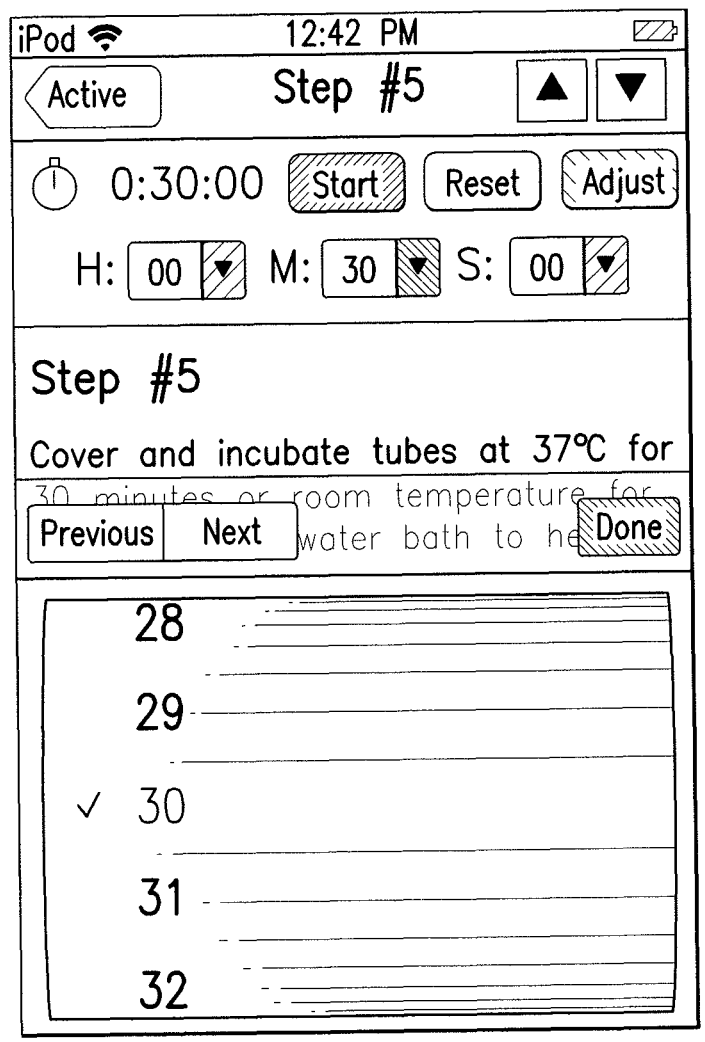
FIG. 9 depicts an exemplary user interface of the protocol interface system.

In an embodiment, each individual step includes any system tools useful or necessary for the step. In addition, the user is presented with a list of product numbers, kit contents, required materials, etc. at the start of running a protocol. In an embodiment, a visual image of a protocol kit is presented, assisting a user in visually inspecting the kit for completeness. For example, the system can provide one or more timers associated with those steps that include timed elements. A exemplary timer is illustrated in FIG. 9. The system can highlight those timers current in use, as well as providing the appropriate interface for interacting with a time (e.g., start, end, pause, and reset buttons). The timer can include a default time, relevant to the particular step, and may be updated by the user. Where multiple timers are in use, the user interface 104 can allow users to select the relevant timer with which to interact. In other embodiments, the user interface 104 provides a customizable timer, allowing users to select an alarm tone and volume, visual cue (e.g., flashing), and warnings or alerts at user selected periods prior to the expiration of the timer. For example, a soft alert sounds approximately five minutes prior to the expiration of the timer and a loud, jarring alert sounds when the timer expires. The user interface 104 can expand timer controls upon user selection, or use a 'flyout' menu to allow users to interact with the timer. A single click on the timer silences the alert and highlights the next step in the protocol. The system can continue to run or function as a background application on a computing device, such that timers and alerts continue to work even if the system is not being currently used. In an embodiment, the user interface 104 is capable of reorienting the text as a user reorients the device ninety or one hundred and eighty degrees.

Figure 10:
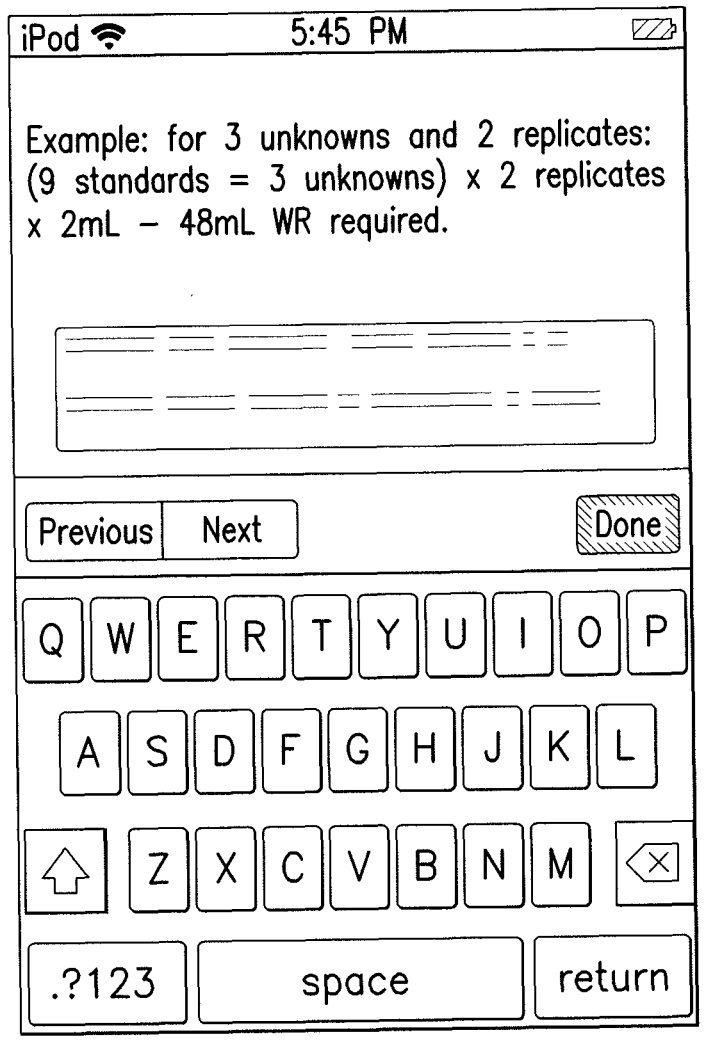
FIG. 10 depicts an exemplary user interface of the protocol interface system.
Figure 11:
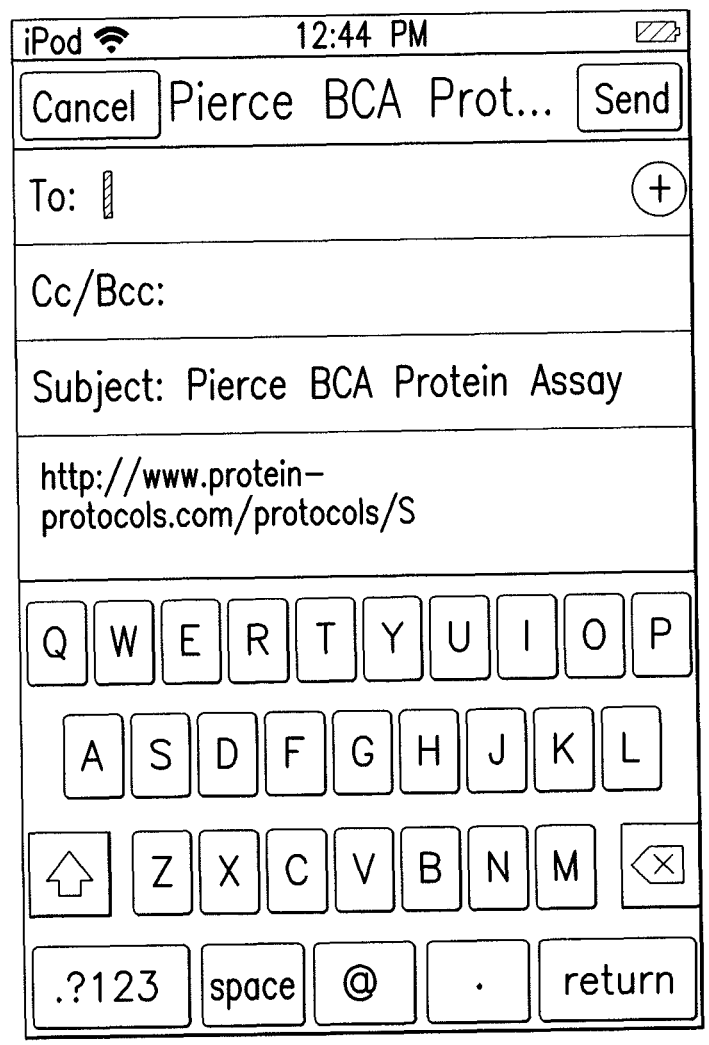
FIG. 11 depicts an exemplary user interface of the protocol interface system.

In another embodiment shown in FIG. 10, the system provides a tool for the entry of text (e.g., a notepad function), allowing users to enter notes regarding the particular step. For example, users may note the location of materials, instrumentation, etc. In another embodiment, these notes are retained with the protocol module and may be reused. In other embodiments, such notes may be posted or provided to the central system 108, for use by additional users. The keyboard and notepad can be presented as a 'flyout' that expands for easy use. In addition, the text entry tool is used in conjunction with a search function, allowing users to search notes, and modules. Other tools may be provided with a protocol. Examples include notes, timer adjustments, date and time, etc. As shown in FIG. 11, these can be sent via email to a specified recipient for formatting, printing and historical reference, etc. This embodiment enables one or more pieces of information about performing a protocol to be automatically recorded with the protocol during use).

In addition, the user interface 104 can include references to remotely located materials relevant to particular steps of a protocol. Such materials can be referenced by use of a hypertext link, where selection of such a link automatically starts a web browser application that opens the web page associated with the referenced material. Alternatively, selection of the link begins a download of referenced material from a remote location. This capability allows for storage of materials at a central system 108, reducing the local memory requirements while retaining accessibility.

Other protocol dynamic features can include a materials checklist. Prior to commencing a protocol, users can review and check off items on a materials checklist, ensuring that all the necessary materials will be at hand to complete protocol prior to commencing the process.

In embodiments, users are able to modify, create and save modules either from the protocol system 100 or the central system 108. The user interface 104 provides a module editor, which allows users to edit and create individual steps, as well as assembling such steps into a complete module. In other embodiments, the user interface 104 will allow users to modify the order of steps within a module, customizing the protocol to fit the individual user's requirements. This is useful for people with several different protocols for a given experiment (i.e., ELISA and Western blot times and steps may change with the particular antibody or substrate used). In an embodiment, the module editor allows users to name, modules, and create steps including brief and detailed descriptions, hyperlinks to resources and default times. Users may be provided with a template or set of templates for use in constructing their own modules. In an embodiment, the module library 106 includes a set of templates, including common stages or steps. Users can select appropriate stages, customizing them for their personal use. Starting with these predefined templates, users can add individual text, timer default settings, and other customizations. In embodiments, the system limits availability of custom features to assist the user in creating usable modules. For example, timers may be limited to non-negative values, logic flow of the stages can be analyzed to determine whether the protocol enters into an infinite loop, wherein the described process forms a logical loop, such that there is no way to finish the protocol. Additional logic checking and expert rules can be utilized to ensure functionality.

In embodiments, the protocol system 100 is able to process more than one protocol at the same time. This is useful where a protocol includes a step that requires significant time without active participation by a user (e.g., cooking or incubating for a length of time). To maximize efficiency, the user can continue with a second protocol while the first runs in the background. In an embodiment, the user interface 104 provides a list of modules or protocols currently running on the system, allowing the user to swap back and forth between or among protocols.

FIGS. 4-11 depict the user interface 104 in English; however, modules and protocols may be translated into any language, enabling the sharing of protocols internationally. For example, a user in France may translate an English language based protocol to French and post it to others at the central system 108. Other users can rate, comment or create additional version of the module, resulting in a French language module.

Additional user interface features include an ability to rotate the display, maximizing the usable screen and effectively allowing the user to customize the view of the protocol. The protocol can incorporate a print function, which prints out user selected steps, notes or information. In an embodiment, the user interface 104 offers the user the option to generate text or formatted file (e.g., PDF or RTF) of protocol information which can be delivered to email or printed.

In an embodiment, the system 100 is capable of communicating downloading or transmitting data to computers and other electronic devices 114. For example, information and user notes associated with a protocol are downloaded to a computerized lab notebook. Information transmitted can include the date and time a protocol was active, timing and results of the protocol, the individual that utilized the protocol as well as any other information related to the protocol.

In an embodiment, the protocol system 100 is used to direct lab equipment. In particular, protocol specific information is transmitted from the protocol system 100 to electronic devices 114 within the lab through a local area network (LAN). For example, protocol specific information such as time and temperature is downloaded to the electronic controls of compatible devices, reducing the likelihood of user error in setting device controls. In an embodiment, the system is used to direct lab equipment remotely through a wide area network (WAN). For example, prior to arriving at the lab or equipment location, the user can direct equipment with heating elements to begin pre-heating. Alternatively, information, e.g., results, from lab equipment can be provided to the system at a remote location. In an embodiment, information may be printed directly from a mobile device, e.g., iPhone®, directly to a printer. In one embodiment, a "smart" appliance may notify the mobile device that an assay has been completed (e.g., a heater has reached required pre-heat setting, a timer on a centrifuge has completed the required centrifugation time, etc.).

In embodiments, the system facilitates capturing potential inventions for subsequent searches, disclosures, etc. In an embodiment, the system is implemented on a mobile device and would allow inventors to quickly and easily jot ideas into a template that would set up the process for a possible patent application. In embodiments, the template would have the inventor indicate why they believe the invention is useful, novel, and non-obvious. Using the entered data, the application could do a quick and very general prior art search, useful in determining whether the invention could be worth pursuing. The system can include functions for organization, memorialization, links to contact information, etc.

Figure 12:
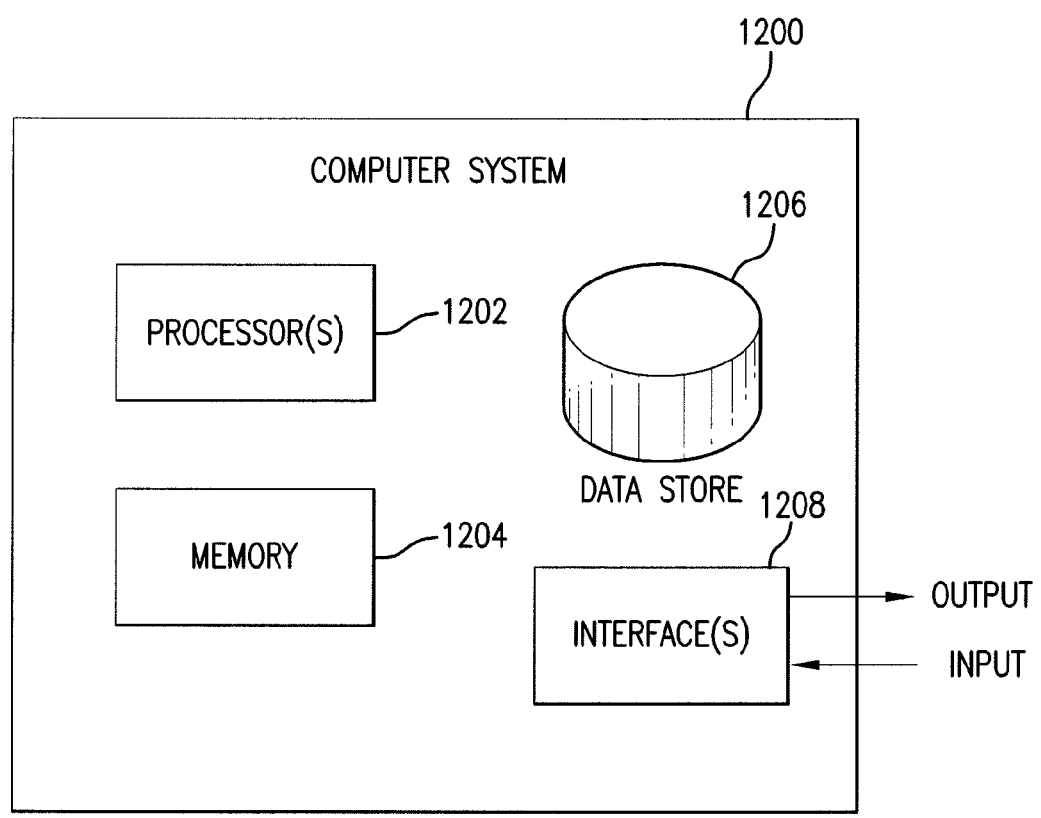
FIG. 12 depicts an exemplary computing system.

FIG. 12 depicts an exemplary computer system 1200 that can be used to implement the protocol system 100. The computer system 1200 can be a laptop, desktop, server, handheld device (e.g., personal digital assistant (PDA), smart phone, etc.), programmable consumer or industrial electronics. As illustrated, the computer system 1200 includes a processor 1202, which can be any various available microprocessors. For example, the processor 1202 can be implemented as dual microprocessors, multi-core and other multiprocessor architectures.

The computer system 1200 includes memory 1204, which can include volatile memory, nonvolatile memory, or both. Nonvolatile memory can include read only memory (ROM) for storage of basic routines for transfer of information, such as during boot or start-up of the computer. Volatile memory can include random access memory (RAM). The computer system can include storage media 1206, including but not limited to magnetic or optical disk drives, flash memory, and memory sticks.

The computer system 1200 incorporates one or more interfaces 1208, including ports (e.g., serial, parallel, PCMCIA, USB, and FireWire) or interface cards (e.g., sound, video, network, etc.) or the like. In embodiments, an interface 1208 supports wired or wireless communications. Input is received from any number of input devices (e.g., keyboard, mouse, joystick, microphone, trackball, stylus, touch screen, scanner, camera, satellite dish, another computer system, etc.). The computer system 1200 outputs data through an output device, such as a display (e.g. CRT, LCD, plasma, etc.), speakers, printer, another computer or any other suitable output device.

Figure 13:
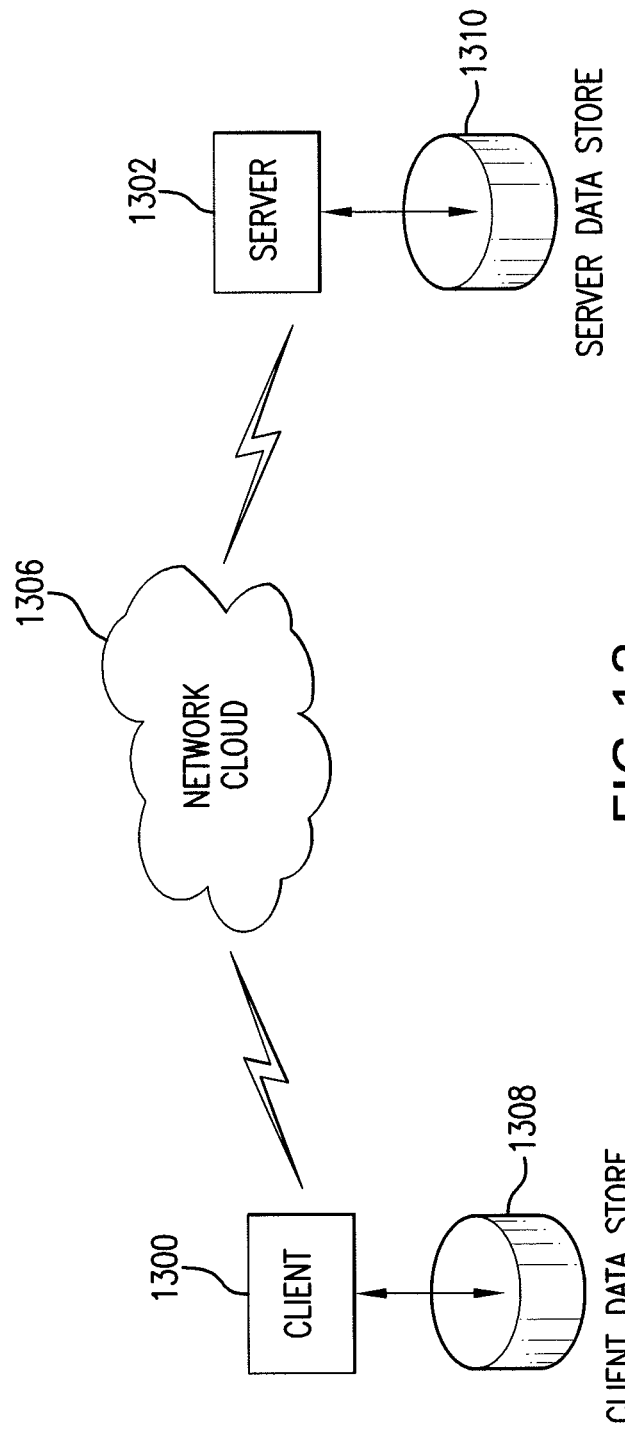
FIG. 13 depicts an exemplary computing environment.

FIG. 13 depicts an exemplary computing environment for the protocol interface system. The environment includes one or more clients 1300, where a client 1300 may be hardware (e.g., personal computer, laptop, handheld device, or other computing devices) or software (e.g., processes or threads). The environment also includes one or more servers 1302, where a server 1302 is software (e.g., thread or process) or hardware (e.g., computing devices), that provides a specific kind of service to a client 1300. The environment can support either a two-tier client server model as well as the multi-tier model (e.g., client, middle tier server, data server and other models). In embodiments, the protocol system 100 is a client 1300 or hosted by a client device, and the central system 108 is a server 1302, or is hosted on a server 1302.

The environment also includes a communication framework 1306 that enables communications between clients and servers. In an embodiment, clients correspond to local area network devices and servers are incorporated in a cloud computing system. A cloud is comprised of a collection of network accessible hardware and/or software resources. The environment can include client data stores 1308 that maintain local data and server data stores 1310 that store information local to the servers 1302, such as the module library 106.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims.

What is claimed is:

1. A laboratory protocol interface computer system comprising at least one processor configured with:
   a dynamic module that specifies a plurality of stages of a protocol for a laboratory procedure, where a selected stage of the plurality of stages includes a procedure instruction for performing the selected stage of the protocol and an associated timer;
   a user interface that enables a user to interact with the protocol specified by the module, where the user interface presents the user with the procedure instruction for the selected stage, enables the user to utilize the associated timer at a selected stage of a protocol controllably displayed, initiated, and terminated at will by the user on the user interface or a remote device to integrate the timer with the instruction for at least one of incubation, reaction, interval, reagent addition, sample removal, aliquot removal, and proceeding to a subsequent task to alert the user in real time during a protocol at the user's discretion and allows the user to customize and/or share the protocol; and
   a module manager that administers the module, such that the module manager modifies the module based at least in part upon user input received through the user interface to customize the protocol.

2. The system of claim 1 where the user interface is implemented on a portable device.

3. The system of claim 1 where the protocol interface system communicates with an electronic device.

4. The system of claim 1 further comprising a module repository of laboratory procedures, where the module manager obtains the module from the module repository.

5. The system of claim 1 where the protocol is a manufacturing method.

6. The system of claim 1 where the protocol is a scientific method.

7. The system of claim 1 where the protocol is selected from the group consisting of a biochemistry, cell biology, molecular biology or protein research laboratory method.

8. The system of claim 1 wherein the timer displays a time for a timed protocol step and indicates when the time has expired.

9. The system of claim 1 wherein the timer permits at least one of a start, end, pause, reset, and default time.

10. The system of claim 1 wherein the timer is customizable.

11. The system of claim 1 wherein the timer processes at least two protocols at the same time.

12. The system of claim 1 wherein the associated timer guides a user through a stage to a next stage of the protocol.

13. A laboratory protocol interface computer system comprising at least one processor configured with
   a dynamic module that specifies a plurality of stages of a protocol for a laboratory procedure, where a selected stage of the plurality of stages includes a procedure instruction for performing the selected stage of the protocol and an associated tool for performing the selected stage;
   a user interface capable of directing the operation of an electronic device, wherein the user interface enables a user to interact with the protocol specified by the module, where the user interface presents the user with the procedure instruction for the selected stage, enables the user to utilize an associated timer at a selected stage of a protocol controllably displayed, initiated, and terminated at will by the user on the user interface or a remote device to integrate the timer with the instruction for at least one of incubation, reaction, interval, reagent addition, sample removal, aliquot removal, and proceeding to a subsequent task to alert the user in real time during a protocol at the user's discretion and allows the user to customize and/or share the protocol; and
   a module manager that administers the module, such that the module manager modifies the module based at least in part upon user input received through the user interface to customize the protocol.

* * * * *